United States Patent
Kunz et al.

(10) Patent No.: US 6,869,652 B2
(45) Date of Patent: Mar. 22, 2005

(54) POROUS POLYMER/CARRIER SOLID PHASE REACTANTS, METHOD FOR PRODUCING SAME AND THE USE THEREOF

(76) Inventors: Ulrich Kunz, Whilhelm-Raabe-Strasse 9, 37520 Osterode (DE); Andreas Kirschning, Berlinerstrasse 51, 38678 Clausthal-Zellerfeld (DE); Ulrich Hoffmann, Maisteig 8, 37154 Northeim (DE)

(*) Notice: Subject to any disclaimer, the term of this patent is extended or adjusted under 35 U.S.C. 154(b) by 100 days.

(21) Appl. No.: 10/221,872
(22) PCT Filed: Mar. 15, 2001
(86) PCT No.: PCT/DE01/01092
§ 371 (c)(1), (2), (4) Date: May 15, 2003
(87) PCT Pub. No.: WO01/68743
PCT Pub. Date: Sep. 20, 2001

(65) Prior Publication Data
US 2004/0062941 A1 Apr. 1, 2004

(30) Foreign Application Priority Data
Mar. 15, 2000 (DE) .......................... 100 12 615

(51) Int. Cl.$^7$ .................................................. B29D 22/00
(52) U.S. Cl. .................... 428/36.5; 428/402; 428/407; 521/30
(58) Field of Search ................ 428/36.5, 402, 428/407; 521/30

(56) References Cited

U.S. PATENT DOCUMENTS 4,130,512 A * 12/1978 Streat ........................ 521/31

* cited by examiner

Primary Examiner—Leszek Kiliman
(74) Attorney, Agent, or Firm—Kriegsman & Kriegsman

(57) ABSTRACT

Disclosed are porous polymer/carrier solid phase reactants which consist of a polymer that consists of fine particles and is situated in the pore space of porous carrier materials. Reactive groups are bound to the polymer. Said groups act as reactants in organic-chemical syntheses. Said solid phase reactants can be produced as bulk material or tubes, plates or rods, can be built in pressure sealed housings and can be used in flow-through apparatuses or microtitration fields for the synthesis of organic products. Potential active agents can be produced at high speed by using the inventive porous polymer/carrier solid phase reactants that can be flown through convectively, whereby production requires only little isolation and cleaning.

21 Claims, 3 Drawing Sheets

Figure 1:
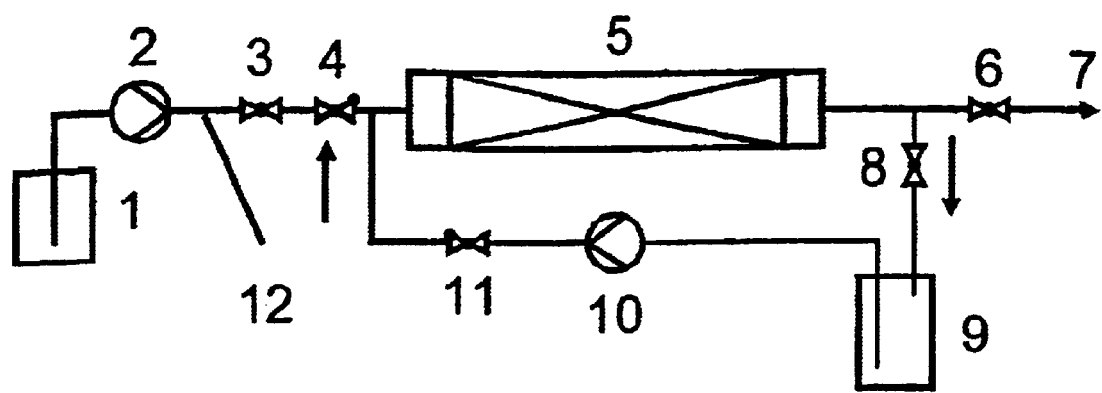

POROUS POLYMER/CARRIER SOLID PHASE REACTANTS, METHOD FOR PRODUCING SAME AND THE USE THEREOF

The invention concerns porous polymer/support solid-phase reactants, a method for their production and their use.

The synthesis of products for organic chemistry, in which the reactants are used in the form of solutions, is the classic mode of operation of organic chemistry and for a long time has been the state of the art. Disadvantages include the handling of large quantities of solvent and the difficult separation of the dissolved products produced from the reaction mixture that is associated therewith.

The use of polymers as anchoring materials for organic reactants represents an improvement. It is an advantage that the substances produced will remain bound to the solid polymer and thus can be well separated from unreacted reactants and byproducts.

Another known example is the synthesis of peptides according to Merrifield (R. B. Merrifield: "Solid Phase Peptide Synthesis", J. Amer. Chem. Soc., Vol. 85, 2149–2154 (1963)). The handling of the polymer, which is present as beads with dimensions in the millimeter range and must be filtered off after their reaction has terminated, is troublesome. The polymer beads used are relatively large, and this adversely affects the transport of the reactant to the active sites of the polymer. Therefore, the reaction times are long.

In order to avoid this disadvantage, the use of powder-form polymers would be more favorable, but handling is adversely affected when powders are used and fine polymer particles can contaminate the products. Another disadvantage of the Merrifield synthesis is the necessary separation of the synthesized product from the polymer. This represents an additional preparative step. In addition, the necessary cleavage reaction may also attack the desired product. Complicating matters is the fact that the analytical tracking of the reaction is difficult, since the synthesized compounds remain bound to the polymer during the synthesis.

The unordered arrangement of the polymer phase as freely moving particles in the reaction medium prevents a controlled flow and can contribute to poor yields and selectivities.

Another disadvantage of conventional materials is the fact that they can be influenced by solvents with various swelling effects. Volumetric changes due to the swelling or shrinking polymer are caused in this way. The flow conditions and transport of the reactants to the polymer-bound reactant in the solid phase are modified in this way.

The use of polymers for anchoring organic reactants and converting them to dissolved products is also in the prior art (D. H. Drewry, D. Coe, S. Poon: Med. Res. Rev. (1999), 19, 97–148). These syntheses are conducted on polymer beads, which have diameters of approximately 0.1 to 1.5 $\mu$m. Here also, it is time-consuming and expensive to separate the polymer phase from the reactants and products. Another disadvantage is that it is difficult to automate this process, because it prolongs the robot-controlled procedure of the operating steps of weighing out the polymer reactants, metering the solid substance and liquids, filtering and separating the reaction products.

Because of the large polymer particles in organic reactions conducted according to the prior art, only a part of the polymer can be actually used in the desired reaction, since the large particles hinder a rapid diffusion of reactants to the bound organic reactants inside the polymer beads. Usually, operation must be conducted with a large (expensive) excess of reactants in order to compensate for this disadvantage.

A material, which combines the favorable properties of solid polymer-bound reactants with the advantages of organic solution chemistry, would be of advantage and, in addition, this material should possess pores that are large enough for convective flow through them.

On the one hand, such a solid-phase reactant should possess fine particles in order to assure a good material transport and thus a good utilization in the synthesis and, simultaneously, it should have dimensions that are as large as possible in order to simplify handling. A solid-phase reactant would also be desirable, which would be suitable for improved methods of high-throughput screening using automated parallel synthesis. A robot-controlled rapid generation of substance libraries of potential new active substances would be possible with such a material.

The object of the invention is thus to provide a polymer/support solid-phase reactant, which overcomes the disadvantages of the prior art.

Surprisingly, this object can be solved with the porous polymer/support solid-phase reactants according to the invention.

The object is solved by creating a porous polymer/support solid-phase reactant wherein a fine-particulate polymer comprised of particles with diameters of 0.001 to 50 $\mu$m, to which organic reactants are bound, are present in the pore volume of a porous support material with pore diameters of 0.1 to 2000 $\mu$m.

In addition, it is preferable that the pore diameter of the porous support material amounts to 10 to 500 $\mu$m.

It is particularly preferred that the particle diameter amounts to 1 to 10 $\mu$m.

It is of advantage that this material has the form of ordered packings, bulk materials, tubes, plates, and rods.

It is also of advantage that these components are [derived] from microfiltration fields.

It is particularly of advantage that the bulk materials are Raschig rings or saddle shapes.

It is particularly advantageous that cross-linked polystyrenes, polyhalostyrenes, polyacrylic acids, polyacrylic acid esters, polyacrylamides, polyacrylonitriles, polyvinyl pyridine, polyvinyl carbazole, polyvinylbenzyl chlorides, polyvinylanilines, polyvinylbenzaldehydes, poly-N-vinyl caprolactams, poly-4-vinyl-1-cyclohexene 1,2-epoxides, poly-3-dimethylaminoacrylonitriles and poly-N,N-dimethylvinylbenzylamines are present as the polymers, either alone or as co-polymers, in the porous support materials.

It is preferred that poly-4-bromostyrene, poly-2-bromostyrene, polyvinylbenzyl bromide and polyvinylbenzyl chloride are used as polyhalostyrenes.

It is additionally preferred that the polymers are cross-linked with divinylbenzene.

It is preferred in each case that the degree of cross-linking amounts to 2 to 55%.

In particular, it is preferred that the embedded polymers possess anchoring groups for organic reactants, such as amino groups, quaternary amino groups, halogen groups, chloromethyl groups, sulfochloride groups, sulfonic acid groups, aldehyde groups, lactam groups, epoxide groups, hydroxy groups, carboxylic acid groups and carboxylic acid halide groups.

It is advantageous that the polymers supporting the organic reactants named in Tables 1 to 7 are present in the pore volume of the support materials.

It is particularly advantageous that glasses, ceramics, glass ceramics, polymers, metals, alloys, substances such as stone, coke and coal are used as the porous support materials.

It is particularly advantageous that pumice stone and silicates are used as stones.

Another subject of the present invention is a method for the production of polymer/support solid-phase reactants according to the invention, wherein a cross-linked polymer is embedded in the support material and this polymer is functionalized with other monomers by a subsequent treatment, whereby the polymer possesses anchoring groups, if needed.

It is preferred according to the invention that the other monomers are introduced by diffusing into the polymer particles and are reacted with a crosslinker.

It is further preferred according to the invention that organic reactants that are known in and of themselves are bound to the anchoring groups. According to the invention, the reactants represented in Tables 1 to 7 are particularly preferred.

Another subject of the present invention is the use of a polymer/support solid-phase reactant according to the invention for conducting addition reactions, oxidations, reductions, epoxidations, halogenations, carbon-carbon coupling reactions, nucleophilic substitutions, dehydrogenations [dehydrations], esterifications, etherifications, acylations, ring openings, cyclizations, isomerizations, electrophilic substitutions, as well as purification steps and multistage reactions by means of the organic reactant present.

It is particularly preferred that the purification reactions involve both "resin capture-and-release" and "scavenger" steps.

It is particularly preferred according to the invention that material synthesis and separation are combined in the polymer/support solid-phase reactant.

Another subject of the present invention is a housing for holding the polymer/support solid-phase reactants according to the invention, characterized in that these latter have a pressure-tight flow-through capacity and that they can be used either individually or in combination in flow-through apparatuses for the synthesis of organic products.

Finally, another subject of the present invention is a device for the use according to the invention of polymer/support solid-phase reactants according to the invention, which [device] consists of a supply tank 1, which is connected to a pump 2 via a line 12, whereby the line is provided subsequently with a shut-off valve 3 and a check valve 4, leads to the upper side of the porous polymer/support solid-phase reactant 5 and is set up on its bottom side so as to branch to metering valve 6 and an outlet for products 7, on the one hand, and is guided, on the other hand, through a pumping cycle, comprised of shut-off valve 8, circulating pump 10 and check valve 11 to the upper side of the porous polymer/support solid-phase reactant.

The use of the solid-phase reactants according to the invention permits new technologies for the production of new substances and their screening for effectiveness. By offering the innovative polymer/support solid-phase reactant with good accessibility to the reactant site by convective through-flow, the material transport is improved and the utilization of the polymer phase is increased. The pore size in the micrometer range permits a higher speed of rinsing and supplying new reaction partners. In this way, a highly efficient method of synthesis is provided for producing new potential active substances.

The polymer/support solid-phase reactants according to the invention, which are described here, can be produced and used in the form of non-uniform packings, ordered packings, as tubes, plates or rods. Of particular advantage is their use in the form of rods or plates, which are incorporated into a housing in a pressure-tight manner and their use in robots for synthesis. By the use of robot technology and the polymer/support solid-phase reactants, a method is provided, which permits producing sufficient quantities of potential active substances as well as new targets for test substances. In combination with methods of chromatographic separation technology, the production of libraries of active substances containing pure substances is possible in a short time. Due to the small polymer particles and the large pores that are simultaneously present, the times for the regeneration of the solid-phase reactants may also be considerably shortened or the regeneration process may be conducted economically for the first time.

The advantages of the polymer/support solid-phase reactants according to the invention are particularly:

After producing the active polymer phase in the pore volume of the support materials, the polymer is immobilized. A cohesive phase is formed, which cannot leave by convective flow through the pore volume.

The loading with polymer is produced by an easily controllable polymerization process.

In this way, a uniform loading of the pore volume of support materials with the active polymer phase is assured.

The loading with polymer can be conducted by selecting the concentration of monomers during the polymerization process. In this way, an optimization is possible with respect to capacity or reaction time.

Conventional methods known in the prior art for activating the polymer phase can be easily conducted. In this way, an adaptation to different synthesis objectives is possible.

The polymer forms a cohesive phase. This phase remains stable in shape by being embedded in the support material, even when there are great changes in the solvatizing properties of the solvent used.

Due to the use of a porous support with large pores for embedding the polymer supporting the reactive groups and the chemical compound of the polymer particles with one another, both small polymer particles as well as large pores can be produced simultaneously. Small pressure losses and high through-flows of reactants are possible with the use of flow-through apparatuses.

A polymers/support solid-phase reactant in piece form or as a rod or plate is more easily handled than a fine particulate powder as a reactant in organic syntheses.

By the form-stable support in combination with a form-fitting housing design, the leaking of a liquid or a dissolved reactant at the edges can be excluded when the latter passes through the solid-phase reactant.

Due to the use of the described solid-phase reactant, the work-up of the reaction products is essentially simpler.

The simple regeneration capacity of the materials, particularly in flow-through apparatuses, shortens the production cycles.

The increase in safety in handling due to the binding of the reactants to the solid polymer phase avoids any contact with low-boiling hazardous substances.

The increased activity due to the binding of the reactant to a dispersed solid matrix increases the productivity.

The following examples explain the invention:

I. Production of Porous Polymer/Support Solid-Phase Reactants.

I.1 Embedding of Cross-Linked Polymers in the Pore Volume of Support Materials a) Polymerization of Vinylbenzyl Chloride and Divinylbenzene.

The production of the porous polymer/support solid-phase reactant according to the invention is described on the basis of polymerization of vinylbenzyl chloride with divinylbenzene.

For the embedding of cross-linked polymers in the pore volume of support materials, a mixture of vinylbenzyl chloride and divynylbenzene in a solvent which well dissolves the monomer, but poorly dissolves the polymer, is produced. After addition of an initiator, e.g., azoisobutyronitrile, one or more porous support material pieces, e.g. rods or plates of porous sintered glass, are placed in the mixture, so that the pieces are completely covered with the reaction mixture. The concentration of the monomers may be varied in order to adjust the polymer load of the support. Then a vacuum is applied briefly, in order to remove air bubbles from the porous support. The polymerization, which leads to the formation of a solid in the pore volume of the support materials, due to the poor solubility of the polymer phase that is formed, begins by heating. After the polymerization has terminated, the support is removed from the reaction solution and cleaned of adhering polymer residues.

For the further increase of the polymer load, it is possible to conduct the described polymerization process repeatedly.

The result of this production process is a polymer phase comprised of bound particles of cross-linked polyvinylbenzyl chloride in the pore volume of the support material. The chloromethyl group can utilized for the coupling of other reactive groups.

b) Polymerization of Other Monomers/Co-Polymers with Divinylbenzene.

In a similar manner, the polymerization of other monomers/copolymers with divinylbenzene is also possible.

Thus, aminostyrenes, styrene, halostyrene, vinylbenzaldehyde, vinylcarbazole, N-vinyl caprolactams, 4-vinyl-1-cyclohexene 1,2-epoxides, vinylpyridine, 3-dimethylaminoacrylonitrile, N,N-dimethylvinylbenzylamine as well as acrylonitrile can be embedded in the pore volume of support materials.

The production of co-polymers is also possible. It is necessary to adapt the type and quantity of the solvent/precipitation agent used to the solution properties of the monomers and polymers.

Other suitable solvents/precipitation agents are alcohols such as methanol, ethanol, propanols, and butanols as well as hydrocarbons and, in several cases, also water. The named solvents can be utilized individually or also in mixtures for the production of porous polymer/support solid-phase reactants. In the case of difficultly soluble monomers, those substances that increase the solubility of monomers, such as, e.g., aromatic substances or other suitable substances, can be added to the reaction mixture.

In the case of polymers, which cannot be embedded in the support or can only be insufficiently embedded by means of a precipitation polymerization, first a cross-linked polystyrene or another polymer that can be well embedded is introduced into the support as described above. Then this product is treated with a solution of the additional polymer in a solvent that swells the polymer that is already present. The additional monomer enters into the gel phase of the polymer that is already present and can be bound in it by known cross-linking methods.

Production processes for porous polymer/support solid-phase reactants are provided by the described methods, which permit fixing a broad palette of anchoring polymers for organic reagents in the pore volume of supports.

In the following, examples of embodiment of the polymer/support solid-phase reactants according to the invention are given, whereby the numbering that is used for the compounds refers to the numbers of the structures that are listed in Tables 1 through 7.

I.2 Activation of Polymers with Anchoring Groups for Organic Reactants in the Porous Phase of Support Materials The following examples of embodiments describe the activation of polymers with anchoring groups for organic reactants in the pore volume of support materials.

a) Amination of Cross-Linked Polyvinylbenzyl Chloride 200 ml of support coated with cross-linked polyvinylbenzyl chloride are reacted with 350 ml of anhydrous toluene in a 1-liter, 3-neck flask. The flask is provided with a thermometer, a reflux condenser, a gas inlet tube, a gas discharge tube, and a drying tube. It is kept at a temperature of 50–60° C. Then anhydrous trimethylamine is slowly introduced. This is carried out by dripping in a 45% aqueous trimethylamine solution into concentrated sodium hydroxide and subsequent drying of the gas flow over solid sodium hydroxide. The gassing is continued for approximately 5 hours, whereby the liquid above the supports is easily stirred. The reaction mixture is left to stand overnight and the gassing process is repeated on the next day. It is then left to stand overnight once more. Then the solution is decanted and replaced by new anhydrous toluene. It is again left to stand overnight. Then the support is removed from the solution and dried in vacuum at 65° C. The supports are treated overnight with 5% hydrochloric acid and then washed with water until they are free of acid. The result of this procedure is a finely divided polymer containing a quaternary amino group in the pore volume of the support material (chloride form of Compound No. 1).

b) Sulfochlorination of Cross-Linked Polystyrene 100 ml of chloroform are mixed with 50 ml of chlorosulfonic acid. At room temperature, 100 ml are added to the dried support materials loaded with crosslinked polystyrene. The mixture is maintained for 24 hours at room temperature with the exclusion of moisture. After the reaction with chlorosulfonic acid has terminated, the chlorosulfonic acid solution is poured off and the polymer-filled support materials are rinsed several times with chloroform and dried in vacuum. The composition of the sulfochlorination mixture and the quantity used can be adapted to the desired degree of sulfochlorination.

The result of this synthesis step is polymer-bound sulforchlorides in the pore volume of porous support materials (Compound No. 67).

c) Methylation of Cross-Linked Polyvinylpyridine 5 g of support containing cross-linked polyvinylpyridine are brought to reaction with a 2× molar quantity of methyl iodide. Instead of methyl iodide, dimethyl sulfate is also suitable. This reaction achieves the production of a basic solid-phase reactant, which can be used for further synthesis. The amination with trimethylamine can be avoided by the use of polyvinylpyridine as the embedded fine-particulate polymer.

I.3 Exchange of the Chloride Group of Polymer/Support Materials for Other Reactive Ions a) Exchange for Iodide The material obtained under Example of Embodiment I.2.a (the chloride form of Compound No. 1) is treated with concentrated (57%) hydroiodic acid. Alternatively, the concentrated hydroiodic acid can be directly added in the hydrolysis step I.2.a. The chloride ions functioning as the counter ions to the quaternary amino functions are exchanged for iodide ions by this step. A highly reactive porous polymer/support solid-phase reactant is made available for organic syntheses with the introduction of the iodide ion into the polymer (Compound No. 72).

c) Exchange of Chloride Ions for Other Reactive Ions

In addition to the above-described example, the exchange of chloride ions for other reactive anions is also possible.

The following listing names several examples:

Borohydride ions (Compound No. 39), cyanoborohydride (Compound No. 40), azide ions (Compound No. 73), cyanide ions (Compound No. 71), rhodanide ions (Compound No. 76), isocyanate ions (Compound No. 83), periodate ions (Compound No. 38), permanganate ions (Compound No.17), as well as the other anions named in Tables 1 to 7.

I.4 Exchange of the Iodide Group for Diacetoxyiodate-(I) Anion

Diacetoxyiodate is introduced into the polymer by reaction of the material obtained in I.3.a) (Compound No. 72) with diacetoxyiodobenzene. A polymer/support solid-phase reactant containing diacetoxyiodate (Compound No. 60) is formed by this synthesis step.

The result of this production method is a support filled with a polymer phase comprised of spherically shaped particles bound to one another, which contains bound reactive groups, which can be utilized as reactants in organic chemistry synthesis. A selection of accessible polymer/support solid-phase reactants as well as the organic reactions that are possible with these can be found in Tables 1 through 7. Anions and cations of the named compounds may be bound in several cases by mutual exchange for new solid-phase reactants. In this way, the number of accessible polymer/support solid-phase reactants is increased considerably.

II. Examples for the Use of Porous Polymer/Support Solid-Phase Reactants in Organic Chemistry Synthesis In order to demonstrate the effectiveness of the polymer/support solid-phase reactants described here, investigations were first conducted, in which the solid-phase reactants were reacted with alkenes.

II.1 Reaction of a Porous Polymer/Support Solid-Phase Reactant with an Olefin in the Case of Free Convective Circular Flow a) Reaction of Polymer-Bound Diacetoxy Iodate with Anethole.

2 g of porous polymer/support solid-phase reactant in the form of Raschig rings, obtained according to Example I.4 (contains Compound No. 60 in the support pore volume), are brought to reaction with a solution of 1 mmol of anethole (1-methoxy-4-propenylbenzene) in anhydrous dichloromethane at room temperature. Iodine and an acetyl group are attached to the double bond of the alkene. The reaction is shown as follows:

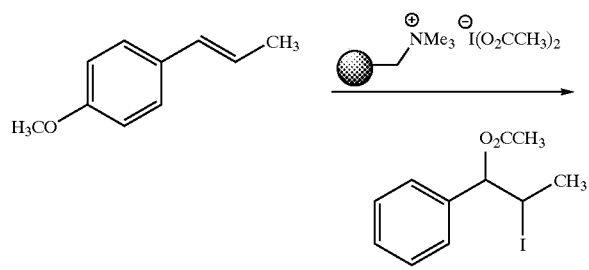

Surprisingly, it was shown in this experiment that a better utilization of the polymer phase could be achieved, in comparison to commercial polymers, due to the use of the porous polymer/support solid-phase reactants described here, which are already in the application form of supports that the solution flows through freely. Whereas one must operate with a 300% excess of reactants in the case of commercial resins, which have particle diameters of up to several millimeters, an excess of only 50% is sufficient in the case of the materials according to the invention. At the same time, the duration of synthesis could be considerably shortened.

The use of the materials according to the invention in the form of components through which liquids can flow by convection in organic chemistry syntheses will be described in the following. Experiments will be described, in which different solid-phase reactants were prepared and used.

II.2. Example for the Use of Porous Polymer/Support Solid-Phase Reactants in the Form of a Component through which Liquids Can Flow by Convection II.2.1. Production of a Porous Polymer/Support Solid-Phase Reactant Containing Borohydride Ions For this purpose, first a polymer/support solid-phase reactant in the form of rods of 5 mm diameter and 10 cm length is incorporated in a pressure-resistant tube without [the possibility of] allowing liquid to leak at the edges. This reactant contains the chloride form of Compound No. 1 as the reactive group. A 1-molar aqueous solution of sodium borohydride is conducted through this rod at room temperature. The test setup is shown schematically in FIG. 1. The named solution is transported from a supply tank 1 via a pump 2 through an opened shut-off valve 3 and a check valve 4 through the porous polymer/support solid-phase reactant 5. After passing through control valve 6, the solution leaves the apparatus at 7. The shut-off valve 8 is closed in this test, and pump 10 is not turned on. 9 is a buffer tank, and 11 is a check valve for protection of the pump.

By conducting the sodium borohydride solution through the rod supporting the chloride ions, the chloride ions are replaced by borohydride ions by means of ion exchange. If chloride ions are no longer detected in the solution exiting at 7, then the metering of the sodium borohydride solution is terminated and methanol is introduced into supply tank 1. Then rinsing is conducted with methanol until the solution leaving the apparatus no longer contains sodium borohydride. Then, rinsing is conducted with dichloromethane or chloroform and drying is completed in vacuum.

The result of this experiment is a polymer/support solid-phase reactant that supports borohydride ions (Compound No. 39), which can be used, e.g., for reductions.

II.2.2. Reduction of Acetophenone with the Use of a Porous Polymer/Support Solid-Phase Reactant Supporting Borohydride Ions The same apparatus is used for this experiment as was described in Example II.2.1. The dried porous polymer/support solid-phase reactant 5 (Compound No. 39) is provided from a supply tank 1 containing methanol, ethanol or propanols at room temperature through pump 2, opened shut-off valve 3 and check valve 4. By opening valve 8 and switching on pump 10, the circulatory flow is placed in operation. After adjusting stable flow conditions by means of valve 6, a quantity of 1 mmol of acetophenone dissolved in alcohol is metered into tank 9 by means of a nozzle. At the same time, shut-off valve 3 and valve 6 are closed and the solution containing the acetophenone at room temperature is circulated through the solid-phase reactant. Samples are removed from tank 9 from time to time and the concentration of the product phenyl ethyl alcohol that is formed is determined. In order to remove the product, valve 6 is opened and solution containing product is removed at 7 from the apparatus. For this purpose, shut-off valve 3 is again opened, and pure solvent is transported into the apparatus until the product that is formed in the apparatus has been completely removed at 7.

The reaction equation for this conversion reads as follows:

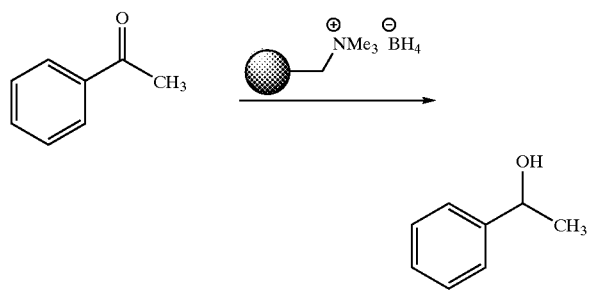

In this example of embodiment, the good flow-through capacity of the porous polymer/support solid-phase reactant described here is shown to be particularly advantageous, along with the good handling capacity, which permits a basically simpler separation and workup than is the case for conventional spherically shaped polymers according to the prior art. The troublesome filtration and batch washing of commercial resins are avoided.

Figure 2:
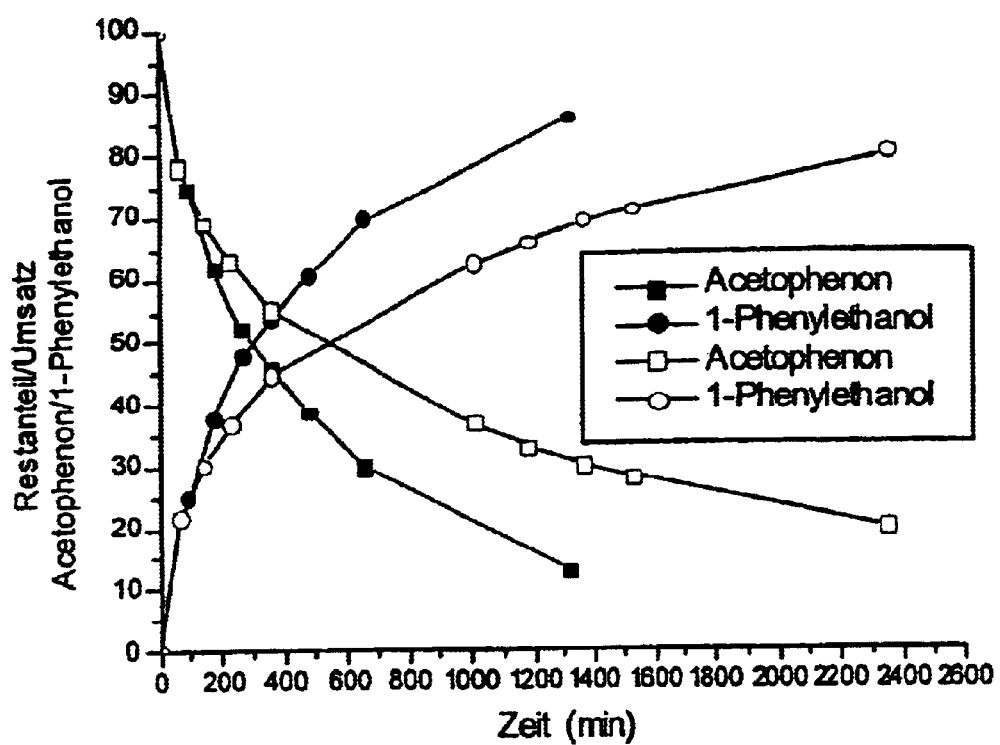

The experimental results obtained are contrasted in FIG. 2 to the results of an experiment, in which a comminuted rod was used in the case of free circular flow by convection. It is clearly shown that when the rod-shaped solid-phase reactant with through flow is used, clearly higher conversions are obtained after shorter times.

The polymer/support solid-phase reactant was utilized for different chemical transformations by means of a device according to the invention as shown in FIG. 1. Here, care was taken to first utilize ionically bound reagents. This procedure also permitted determining the recycling of the reactors for the same chemical transformations as well as for different ones. The following reactions could be produced sequentially with a microreactor. In the following Table A, other examples of reactions, which were conducted with the polymer/support solid-phase reactants according to the invention are listed.

Taken individually, these are:

1. Reduction of acetophenone to 1-phenyl ethanol with immobilized borohydride ions (Example 1).

2. TEMPO-mediated oxidation of cyclohexanol to cyclohexanone and a steroid alcohol to the ketone with the immobilized bromate complex (Examples 2 and 3).

3. Desilylation of a steroid with the immobilized fluoride ion and formation of the alcohol (Example 4).

4. Reductive amination of the ketone and formation of the benzylamine with utilization of the immobilized borohydride ion (Example 5).

5. Substitution reactions of benzyl bromide with immobilized azide and cyanide ions (Examples 6 and 7).

6. Substitution reaction of octyl iodide with the immobilized thiocyanate ion (Example 8).

TABLE A

| Example | Educt | Reagent | Product | Conversion (Purity) |
|---|---|---|---|---|
| 1 | Ph-C(=O)-Me | ⊕NMe₃ BH₄⊖ MeOH, 60° C., 6 h | Ph-CH(OH)-Me | >99% (NMR-pure) |
| 2 | cyclohexanol | ⊕NMe₃ Br(OAc)₂⊖ kat. TEMPO, CH₂Cl₂, rt, 6 h kat = cat. | cyclohexanone | >99% (NMR-pure) |
| 3 | steroid with OSiEt₃ and 3-OH | ⊕NMe₃ Br(OAc)₂⊖ kat. TEMPO, CH₂Cl₂, rt, 6 h 12, rt kat = cat. | steroid with OSiEt₃ and 3-keto | >99% (NMR-pure) |

TABLE A-continued

| Example | Educt | Reagent | Product | Conversion (Purity) |
|---|---|---|---|---|
| 4 | (steroid with Me, OH, H, =O) | ⊕NMe₃ F⊖ on support; MeOH, rt, 24 h | (steroid product) | 90% (contains traces of educt) |
| 5 | (steroid with Me, OH, H, =O) | ⊕NMe₃ BH₄⊖ on support; BnNH₂, MeOH, 12 h, rt | (BnHN-steroid product) | >85% (contains traces of the alcohol) |
| 6 | PhCH₂Br | ⊕NMe₃ N₃⊖ on support; C₆H₆, 70° C., 12 h | PhCH₂N₃ | >99% (NMR-pure) |
| 7 | PhCH₂Br | ⊕NMe₃ CN on support; C₆H₆, 70° C., 12 h | PhCH₂CN | >99% (NMR-pure) |
| 8 | CH₃(CH₂)₇I | ⊕NMe₃ SCN⊖ on support; C₇H₈, 70° C., 6 d | CH₃(CH₂)₇SCN | 85% (and 15% educt) | kat = cat.

Several other reactions will be described in the following, which were conducted with the device according to the invention using the polymer/support solid-phase reactants according to the invention.

1. Reduction of Acetophenone (General Instructions for NaBH₄ Reduction)

The chloride form of the microreactor was treated sequentially with NaOH (10 mmol in 10 mL of water), demineralized water (10 mL), sodium borohydride (1 g in 10 mL of water), demineralized water (10 mL) and methanol (10 mL). A solution of acetophenone (0.5 mmol in 10 mL of methanol) was cycled through the reactor at 60° for over 6 h until the reaction completely terminated. The reactor was rinsed with methanol (10 mL) and the solvent was removed in vacuum. Yield of 1-phenyl ethanol >99%.

2. Oxidation of Cyclohexanol (General Instructions for TEMPO-Catalyzed Oxidation)

The chloride form of the microreactor was treated sequentially with NaOH (10 mmol in 10 mL of water), demineralized water (10 mL), HBr (2 N, 10 mL), demineralized water (10 mL), anhydrous methanol (10 mL) and anhydrous dichloromethane. Then a solution of iodobenzene diacetate (1.5 mmol in 10 mL of anhydrous dichloromethane) was circulated by the pump through the reactor at room temperature for 12 h. The reactor was washed with anhydrous dichloromethane (10 mL). A solution of cyclohexanol (0.125 mmol in 10 mL of anhydrous dichloromethane) was brought to reaction in the column with a catalytic quantity of TEMPO under argon until the conversion was complete, 86 h). The reactor was rinsed with dichloromethane (10 mL) and the solvent was drawn off in vacuum. Yield of cyclohexanone: >99%).

3. Oxidation of Steroids

[Operation was conducted] analogously to paragraph 2. Steroid alcohols were brought to reaction. Yield of steroid ketones: 99%.

4. Desilylation (of a Steroid)

The chloride form of the microreactor was treated sequentially with NaOH (10 mmol in 10 mL of water), demineralized water (10 mL), HF (2 N, 10 mL) and anhydrous methanol (15 mL). A solution of O-triethylsilyl-protected steroid (0.5 mmol in 10 mL of methanol) was brought to reaction in through-flow for 24 h. The reactor was rinsed with methanol (10 mL) and the solvent was then removed in vacuum. Yield of desilylated steroid: >90% together with traces of the initial material.

5. Reductive Amination of a Steroid

The chloride form of the microreactor was sequentially treated with NaOH (10 mmol in 10 mL of water), demineralized water (10 mL), sodium borohydride (1 g in 10 mL of water), demineralized water (10 mL) and methanol (10 mL).

A solution of steroid ketone and benzylamine (0.5 mmol each in 10 mL of methanol) was circulated through the reactor for more than 12 h at room temperature until complete conversion occurred. The reactor was washed with methanol (10 mL) and the solvent was removed in vacuum. Yield: >85%.

6. General Instructions for the Synthesis of Azides

The chloride form of the microreactor was treated sequentially with NaOH (10 mmol in 10 mL of water), demineralized water (10 mL), sodium azide (1 g in 10 mL of water), demineralized water (10 mL), methanol (10 mL) and benzene (10 mL).

A solution of benzyl bromide (0.5 mmol in 10 mL of benzene) was pumped through the reactor for more than 12 h at 70° C. for the complete reaction. After the solvent was removed, benzyl azide was obtained in a yield of >99%.

7. Synthesis of Benzyl Cyanide

Analogously to paragraph 6, but, of course with the use of sodium azide, benzyl cyanide in a yield of >99% was obtained with through-flow at 70° C. after 12 h of reaction.

8. Synthesis of Octyl Thiocyanate

Octyl thiocyanate in a yield of >85% along with 15% octyl iodide was obtained with the use of sodium thiocyanate (1 g in 10 mL of water) with operation analogous to paragraph 6, from octyl iodide (0.5 mmol in 10 mL of benzene) after a reaction time of 6 d at 70° C., rinsing of the reactor with benzene (10 mL) and removal of the solvent.

After synthesis has been carried out, the reactant column can be again regenerated. For this purpose, it is first loaded again with chloride ions by passing through a dilute hydrochloric acid solution, which displaces the byproducts of the organic synthesis that are bound to the solid phase. After rinsing with water, the solid-phase reactant can again be loaded with borohydride ions.

After regeneration has been conducted, e.g., the solution of another ketone or another substance to be reduced by borohydride ions can be pumped through the porous polymer/support solid-phase reactant and another substance of a substance library can be produced. By this technique, extensive substance libraries containing potential new active ingredients or building blocks for their synthesis can be successfully produced in a short time. Of course, the combined connection of several flow-through components with porous polymer/support solid-phase reactants to form a synthesis robot, which can also conduct multistage syntheses, is possible.

The porous polymer/support solid-phase reactants described here and their use represent only selected procedures for indicating the possibilities in principle. A large number of functionalizing reactions conducted on commercially-available pure polymers are known from the prior art. These can be transferred to the polymer/support solid-phase reactants described here and permit the person of average skill in the art to considerably broaden the application potential.

For example, the polymer/support solid-phase reactant, which contains cross-linked vinylbenzyl chloride in the support, may also be used in the Merrifield synthesis. In this way, a possibility is provided which permits this synthesis operation with high throughput and thus reduces the time involved. The embedding of the polymers in the support materials is produced according to the method described here via a precipitation polymerization. Other methods (emulsion polymerization, the sol-gel technique, polymerization with the use of supercritical solvent) may also be suitable for producing fine-particulate solid polymer phases in the pore volume of porous supports and thus can be used for the production of the polymer/support solid-phase reactants presented here.

The structures of active polymers in the porous polymer/support solid-phase reactants are indicated with the structural formulas, numbers 1 to 113, in Tables 1 to 7. In these illustrations, the shaded circle indicates the backbone of the crosslinked polymer chain.

Figure 3:

FIG. 3 represents a scanning electron micrograph of a cross section through the porous polymer/support solid-phase reactants described here. The polymer particles that are bound together can be clearly seen in the pore volume along with the large pores that are present between the particles, and which permit a good flow through the solid-phase reactant by convection. The spherically-shaped polymer particles bound together and forming a solid-phase reactant can be clearly seen. The diameters of the polymer particles bound together lie in the micrometer range, while the diameters of the pores between these particles also lie in the micrometer range.

TABLE 1

Bases

| Number | Structure | Reactions |
|---|---|---|
| 1 | 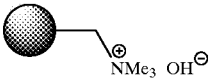 $NMe_3$ $OH^\ominus$ | Deprotonations; removal of acidic compounds from reaction mixtures; |
| 2–5 | 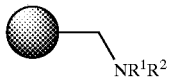 $NR^1R^2$ | Deprotonations, purification of reaction mixtures (carboxylic acid chlorides, sulfonic acid chlorides, sulfonic acids, carboxylic acids, isocyanates); removal of acidic compounds from reaction mixtures; |
| 6–8 | $R^1 = R^2$ H, $CH_3$, $CH_2CH_3$, $CH(CH_3)_2$ $R^1$ = H und $R^2 = CH_3CH_2CH_3$, $CH_2CH_2NH_2$ und = and | |

TABLE 1-continued

Bases

| Number | Structure | Reactions |
|---|---|---|
| 9 | 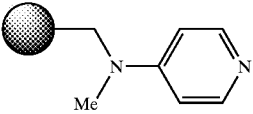 | Deprotonations, acylations and sulfonylations; removal of acidic compounds from reaction mixtures; |
| 10 | 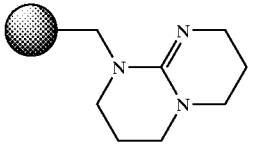 | Deprotonations; removal of acidic compounds from reaction mixtures; synthesis of aryl triflates; |
| 11 | 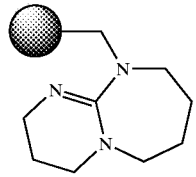 | Deprotonations; removal of acidic compounds from reaction mixtures; |
| 12 | 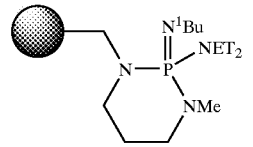 | Strong base, deprotonations; removal of acidic compounds from reaction mixtures |
| 13 | 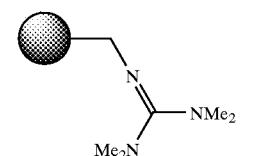 | Base, deprotonations; removal of acidic compounds from reaction mixtures; |
| 14 | 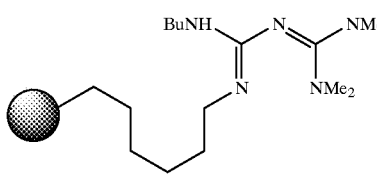 | Base, deprotonations; removal of acidic compounds from reaction mixtures; |
| 15 | 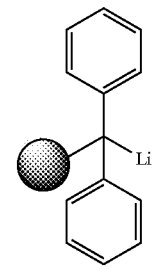 | Deprotonations; |
| 16 | 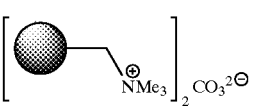 | Deprotonations; removal of acidic compounds from reaction mixtures; |

TABLE 2

Oxidation agents

| Number | Structure | Reactions |
|---|---|---|
| 17 | ●—NMe$_3^{\oplus}$ MnO$_4^{\ominus}$ | Oxidation of alcohols and aldehydes; |
| 18 | ●—NMe$_3^{\oplus}$ RuO$_4^{\ominus}$ | Oxidation of alcohols and aldehydes; |
| 19 | ●—CO$_3$H | Epoxidation of alkenes; Baeyer-Villiger oxidation; Oxidation of sulfides to sulfoxides and phosphanes to phosphine oxide; |
| 20 | ●—SO$_4$H | Epoxidation of alkenes; Baeyer-Villiger oxidation; Oxidation of sulfides to sulfoxides and phosphanes to phosphine oxide; |
| 21 | ●—AsO$_3$H$_2$ | Baeyer-Villiger oxidation; |
| 22 | ●—SeO$_2$H | Oxidation of benzyl alcohols to benzaldehydes and hydroquinones to quinones; |
| 23/24 | ●—I(O$_2$CCH$_3$)$_2$ <br> ●—I(O$_2$CCF$_3$)$_2$ | Alpha-oxidation of ketones; oxidative 1,2-aryl migration of alkyl aryl ketones; |
| 25 | ●—NMe$_3^{\oplus}$ OO$^{\ominus}$ | Epoxidation of alkenes |
| 26 | ●—pyrazole(Ph)—N(CH$_3$)$^{\oplus}$ HCrO$_4^{\ominus}$ | Oxidation of alcohols and aldehydes; |
| 27 | ●—pyrazole(Ph)—NH$^{\oplus}$ ClCrO$_3^{\ominus}$ | Oxidation of alcohols and aldehydes; |
| 28 | ●—pyrazole(Ph)—N—CrO$_2$OH | Oxidation of alcohols and aldehydes; |
| 29 | ●—NMe$_3^{\oplus}$ CrO$_4$H$^{\ominus}$ | Oxidation of alcohols and aldehydes; |
| 30 | ●—NMe$_3^{\oplus}$ CrO$_4$H$^{\ominus}$ | Oxidation of alcohols and aldehydes; |

TABLE 2-continued

Oxidation agents

| Number | Structure | Reactions |
|---|---|---|
| 31 | 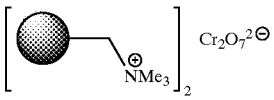 | Oxidation of alcohols and aldehydes; |
| 32 | 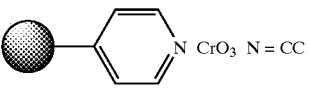 | Oxidation of alcohols and aldehydes; |
| 33 | 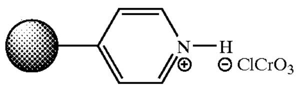 | Oxidation of alcohols and aldehydes; |
| 34 | 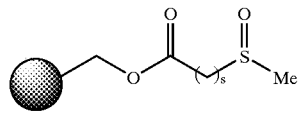<br>(COCl)$_2$, NEt$_2$ | Swern oxidation; |
| 35 | 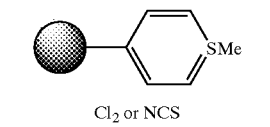<br>Cl$_2$ or NCS | Corey oxidation; |
| 36 | 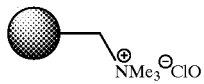 | Oxidation of alcohols and aldehydes; |
| 37 | 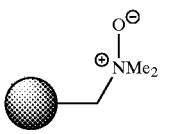 | Oxidation of primary alkyl halides to aldehydes; |
| 38 | 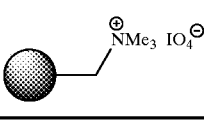 | Periodate cleavage of 1,2-diols; oxidation of sulfides; |

TABLE 3

Reducing agents

| Number | Structure | Reactions |
|---|---|---|
| 39 | 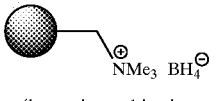<br>(in part in combination with metal salts, such as CuSO$_4$, NiCl$_2$ | Reductions of carbonyl groups, acid chlorides, alkyl and benzyl halides as well as the corresponding sulfonic acid esters, nitro groups, nitroalkenes, aryloximes; azides; |
| 40 | 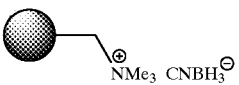 | Reduction of imines; utilization for the reductive amination of aldehydes and ketones; |
| 41 | 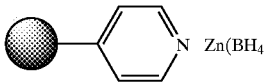 | Reduction of aldehydes in the presence of ketones; |

TABLE 3-continued

Reducing agents

| Number | Structure | Reactions |
|---|---|---|
| 42 | ●—⟨pyridine⟩—N Zr(BH$_4$)$_4$ | Reduction of aldehydes and ketones |
| 43 | ●—CH$_2$—N$^+$Me$_3$ (S$_2$O$_3$)$_{0.5}$$^-$ | Removal of halogens as well as of iodine (III) and iodine (V) compounds from reaction mixtures; |
| 44 | ●—CH$_2$—SnBu$_2$H | Reduction of alkyl halides, xanthates; |

TABLE 4

Halogenation/dehydrating agents

| Number | Structure | Reactions |
|---|---|---|
| 45 | ●—CH$_2$—N$^+$(Me)(Me)—(CH$_2$)$_3$—N=C=NR, Cl$^-$ | Formation of peptide, amide and ester bonds; |
| 46 | ●—CH$_2$—(benzotriazole)—OH | Formation of peptide, amide and ester bonds; Transfer of protective groups (Fmoc, Cbz, Boc); preparation of N-hydroxysuccinimide esters; |
| 47 | ●—CH$_2$—NH—C(O)—(phthalimide)NH | Amination of alcohols via the Mitsunobu reaction and hydrazinolysis; |
| 48 | ●—PPh$_2$/CCl$_4$ | Chlorination of alcohols; dehydration of carboxylic acid amides and oximes to nitriles |
| 49 | ●—PPh$_2$/Cl$_2$ | Chlorination of alcohols |
| 50 | ●—PPh$_2$/Br$_2$ | Formation of bromohydrins from epoxides; dehydration of ureas and thioureas to carbodiimides; |
| 51 | ●—PPh$_2$/I$_2$ | Iodination of alcohols; formation of iodohydrins from epoxides; |
| 52 | ●—⟨pyridine⟩—N·Br | Bromination of alkenes, alkynes; α-bromination of carbonyl compounds; |
| 53 | ●—CH$_2$—N$^+$Me$_3$ Br$_3$$^-$ | Brominations of alkenes, alkynes; α-bromination of carbonyl compounds; |

TABLE 4-continued

Halogenation/dehydrating agents

| Number | Structure | Reactions |
|---|---|---|
| 54 | pyridinium-N-R with Br$_3^-$ on resin | Brominations of alkenes, alkynes; α-bromination of carbonyl compounds; |
| 55 | resin-CH$_2$-NMe$_3^+$ (BrCl$_2$)$^-$ | 1,2-cohalogenation of alkenes, alkynes; |
| 56 | pyridinium-N-R with BrCl$_2^-$ on resin | 1,2-cohalogenation of alkenes, alkynes; |
| 57 | pyridinium-NR with (ICl$_2$)$^-$ on resin | 1,2-cohalogenation of alkenes, alkynes; |
| 58 | resin-CH$_2$-NMe$_3^+$ Br(OAc)$_2^-$ | 1,2-cohalogenation of alkenes, alkynes; |
| 59 | pyridinium-N-Me with Br(OAc)$_2^-$ on resin | 1,2-cohalogenation of alkenes, alkynes; |
| 60 | resin-CH$_2$-NMe$_3^+$ I(OAc)$_2^-$ | 1,2-cohalogenation of alkenes, alkynes; iodination of terminal alkynes; |
| 61 | pyridinium-N-Me with I(OAc)$_2^-$ on resin | 1,2-cohalogenation of alkenes; |
| 62 | resin-CH$_2$-NMe$_3^+$ I(O$_2$CCF$_3$)$_2^-$ | 1,2-cohalogenation of alkenes; |
| 63 | pyridinium-N-Me with I(O$_2$CCF$_3$)$_2^-$ on resin | 1,2-cohalogenation of alkenes; |
| 64 | resin-CH$_2$-NMe$_3^+$ I(N$_3$)$_2^-$ | 1,2-iodoazidation of alkenes; |
| 65 | pyridinium-N-Me with I(N$_3$)$_2^-$ on resin | 1,2-cohalogenation of alkenes; |
| 66 | resin-CH$_2$-(2-Me-imidazolium) Br$_3^-$ | Brominations of alkenes; α-bromination of carbonyl compounds; |
| 67 | resin—SO$_2$Cl | α-chlorination of carbonyl groups; alkylation of amines via the sulfonic acid ester; |

TABLE 4-continued

Halogenation/dehydrating agents

| Number | Structure | Reactions |
|---|---|---|
| 68 | 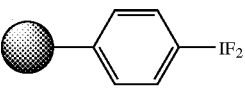 | Fluorination of aryl alkenes to geminal difluorides; |
| 69 | 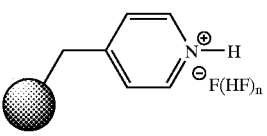 | Fluorination of alcohols, hydrofluorination of alkenes and alkynes; |
| 70 | 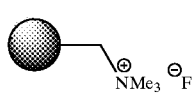 | Fluorination of alkyl halides and sulfonic acid esters; |

TABLE 5

Nucleophilic reagents

| Number | Structure | Reactions |
|---|---|---|
| 71 | 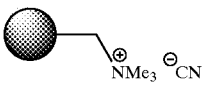 | Substitution with cyanide; |
| 72 | 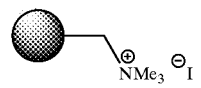 | Substitution with iodide; |
| 73 | 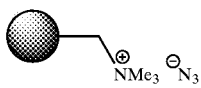 | Substitution with azide; |
| 74 | 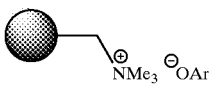 | Substitution with phenolate; |
| 75 | 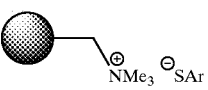 | Substitution with thiophenolate |
| 76 | 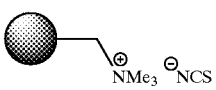 | Substitution with thiocyanate; |
| 77 | 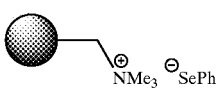 | Substitution with selenophenolate; |
| 78 | 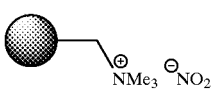 | Substitution with nitrite; |
| 79 | 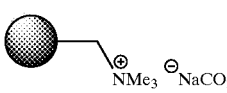 | Substitution with hydroxyl anion; |
| 80 | 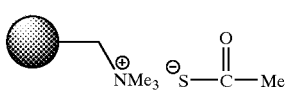 | Substitution with thioacetic acid; |

TABLE 5-continued

Nucleophilic reagents

| Number | Structure | Reactions |
|---|---|---|
| 81 | (resin-CH₂-bicyclic guanidine) ⁺H ⁻OAr | Substitution with phenolate; |
| 82 | (resin-CH₂-N⁺Me₃) ⁻O₂CAr | Substitution with aryl carboxylic acids; |
| 83 | (resin-CH₂-N⁺Me₃) ⁻NCO | Substitution with isocyanate; |

TABLE 6

C—C-coupling reagents

| Number | Structure | Reactions |
|---|---|---|
| 84 | (resin-P(Ph)(Ph)=R) | Wittig olefination; |
| 85 | (resin-CH₂-N⁺Me₃) (R¹O)(R¹O)P(=O)-C⁻H-X | Horner-Emmons olefination; |
| 86 | (resin-CH₂-O-P(=O)(OR)-CH₂-C(=O)-OR') | Horner-Emmons olefination; |
| 87 | (resin-S(=CH₂)-OR) | Synthesis of oxiranes from aldehydes; |
| 88 | (resin-CH₂-N⁺Me₃) ⁻BH₄  Ni(II)-Salze | Addition of alkyl iodides and α-bromocarboxylic acids/esters to alkenes; |
| 89 | (resin-CH₂-SnBu₂-SnBu₂-CH₂-resin) | (in the presence of a radical initiator) addition of alkyl halides to alkynes, cyclization of unsaturated alkyl halides |

TABLE 6-continued

C—C-coupling reagents

| Number | Structure | Reactions |
|---|---|---|
| 90 | 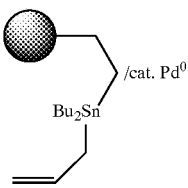 | (in the presence of a radical initiator) allylation of alkyl halides; |
| 91 | 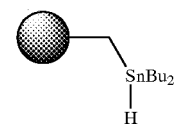 | (in the presence of a radical initiator) addition of alkyl halides to alkynes, cyclization of unsaturated alkyl halides; |

TABLE 7

Diverse functionalities

| Number | Structure | Reactions |
|---|---|---|
| 92 | <br>diethyl azodicarboxylate (DEAD) | Mitsunobu reaction; |
| 93 | 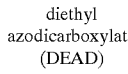 | Mitsunobu reaction; |
| 94 | 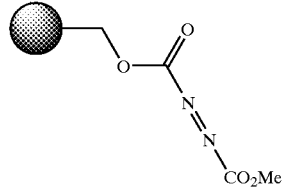 | Diazo transfer to β-dicarbonyl compounds; |
| 95 | 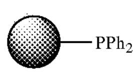 | Isomerization of (Z)-nitroolefins to (E)-nitroolefins; |
| 96 | 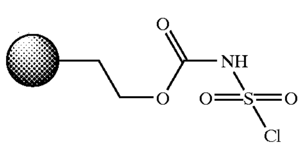 | Polymer-bound Burgess reagents; Elimination of alcohols; cyclodehydration of β-hydroxyamides and β-hydroxythioamides; |
| 97 | 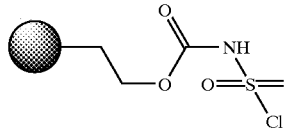 | Lewis acid; immobilization of unsaturated carbonyl compounds with the formation of enol ethers and subsequent Diels-Alder cyclo additions; |
| 98 | 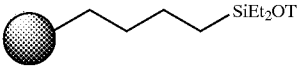 | Removal of amines from reaction mixtures; |

TABLE 7-continued

Diverse functionalities

| Number | Structure | Reactions |
|---|---|---|
| 99 | [resin]-CH₂-O-C(=O)-Cl | Removal of amines, alcohols from reaction mixtures; immobilization of nitrogen-containing heteroaromatic substances; |
| 100 | [resin]-NCO | Removal of amines and alcohols from reaction mixtures; |
| 101 | [resin]-CHO | Removal of amines, hydrazines, reducing agents, C-nucleophilic substances, organometallic reagents and ketoesters from reaction mixtures; |
| 102 | [resin]-SeLi | Bromoselenations of alkenes; |
| 103 | [resin]-SeLi | Synthesis of alkenes from alkyl iodides; |
| 104 | [resin]-CH₂-O-C₆H₄-CH=N-N₂ | Removal of carboxylic acids from reaction mixtures; |
| 105 | [resin]-CH₂-NH-CH₂CH₂-SH | Removal of α-thiocarboxylic acids from reaction mixtures; |
| 106 | [resin]-NMe₃⁺  ⁻O₂C-CH₂CH₂-S-CH₂CH₂-CO₂H | Reductive purification by ozonolyses; |
| 107 | [resin]-CH₂-N(Me)-C(=NMe)-N(Me)₂ (tetramethylguanidine) | Removal of tricarboxyethylphosphines and phosphine oxides from reaction mixtures; |
| 108 | [resin]-CH₂-NH-C(=S)-NH₂ | Removal of α-halogenated carbonyl compounds from reaction mixtures; |
| 109 | [resin]-C₆H₄-S(=O)₂-NHNH₂ | Removal of aldehydes and ketones from reaction mixtures; |
| 110 | [resin]-CH₂-O-(3-pyridyl) | Ring-closing reactions analogous to the Robinson anellation; |

TABLE 7-continued

Diverse functionalities

| Number | Structure | Reactions |
|---|---|---|
| 111 | (structure with N, two CH₂CH₂OH groups on bead) | Removal of boric acid esters from reaction mixtures (Suzuki reactions); |
| 112 | (bead-CH₂-C(O)-NH-N=CH-R structure) | Synthesis of pyrazolones; |
| 113 | (bead-phenyl-NH-C(O)-CH₂-CH₂-phenyl-SH structure) | Removal of alkylation agents such as methyl iodide from reaction mixtures; |

LIST OF REFERENCE NUMBERS

1 = supply tank
2 = pump
3, 8 = shut-off valve
4, 11 = check valve
5 = porous polymer/support solid-phase reactant
6 = metering valve
7 = outlet for products
9 = tank
10 = circulating pump
12 = line

What is claimed is:

1. Polymer/support solid-phase reactants, hereby characterized in that a fine particulate polymer comprised of particles with diameters of 0.001 to 50 µm to which organic reactants are bound is present in the pore volume of a porous support material with pore diameters of 0.1 to 2000 µm.

2. The polymer/support solid-phase reactant according to claim 1, further characterized in that the pore diameter of the porous support material amounts to 10 to 500 µm.

3. The polymer/support solid-phase reactants according to claim 1, further characterized in that the particle diameter amounts to 1 to 10 µm.

4. The polymer/support solid-phase reactant according to claim 1, further characterized in that these have the form of ordered packings, bulk materials, tubes, plates and rods.

5. The polymer/support solid-phase reactants according to claim 4, further characterized in that these are components from microtitrating fields.

6. The polymer/support solid-phase reactants according to claim 4, further characterized in that the bulk materials are spheres, Raschig rings or saddle-shaped pieces.

7. The polymer/support solid-phase reactants according to claim 1, further characterized in that cross-linked polystyrenes, polyhalostyrenes, polyacrylic acids, polyacrylic acid esters, polyacrylamides, polyacrylonitriles, polyvinylpyridines, polyvinyl carbazoles, polyvinylbenzyl chlorides, polyvinyl anilines, polyvinylbenzaldehydes, poly-N-vinyl caprolactams, poly-4-vinyl-1-cyclohexene 1,2-epoxides, poly-3-dimethylaminoacrylonitriles and poly-N,N-dimethylvinylbenzylamines are present in the porous support materials as polymers, either alone or as copolymers.

8. The polymer/support solid-phase reactants according to claim 7, further characterized in that poly-4-bromostyrene, poly-2-bromostyrene, polyvinylbenzyl bromide and polyvinylbenzyl chloride are used as polyhalostyrenes.

9. The polymer/support solid-phase reactants according to claim 7, further characterized in that the polymers are cross-linked with divinylbenzene.

10. The polymer/support solid-phase reactants according to one of claims 7 to 9, further characterized in that the degree of cross-linking amounts to 2 to 55%.

11. The polymer/support solid-phase reactants according to claim 1, further characterized in that the embedded polymers possess anchoring groups for organic reactants selected from, amino groups, quaternary amino groups, halogen groups, chloromethyl groups, sulfochloride groups, sulfonic acid groups, aldehyde groups, lactam groups, epoxide groups, hydroxy groups, carboxylic acid groups and carboxylic acid halide groups.

12. The polymer/support solid-phase reactants according to claim 1, further characterized in that the polymers present in the pore volume of the support material support organic reactants.

13. The polymer/support solid-phase reactants according to claim 1, further characterized in that the porous support materials are glasses, ceramics, glass ceramics, polymers, metals, alloys, stones, coke or coral or other porous substances.

14. The polymer/support solid-phase reactants according to claim 13, further characterized in that the stones are pumice stone and silicates.

15. A method for the production of polymer/support solid-phase reactants according to claim 1, hereby characterized in that across-linked polymer is embedded in the support material and this polymer is functionalized by a subsequent treatment with other monomers, whereby the polymer possesses anchoring groups, if necessary.

16. The method according to claim 15, further characterized in that the other monomers are introduced by diffusing into the polymer particles and then these are reacted with a cross-linker.

17. The method according to one of claim 15 or 16, further characterized in that organic reactants that are bound to the anchoring groups.

18. Use of a polymer/support solid-phase reactant according to claim 1 for conducting addition reactions, oxidations, reductions, epoxidations, halogenations, carbon-carbon coupling reactions, nucleophilic substitutions, dehydrogenations dehydrations, esterifications, etherifications, acylations, ring openings, cyclizations, isomerizations, electrophilic substitutions, as well as purification steps and multi-stage reactions by means of the organic reactants present.

19. The use according to claim 18, further characterized in that the purification reactions involve resin capture-and-release scavenger steps.

20. The use according to claim 18, further characterized in that the substance is synthesized and separated in a combined manner in the polymer/support solid-phase reactant.

21. A housing for the uptake of the polymer/support solid-phase reactants according to claim 1, hereby characterized in that a substance can flow through it in a pressure-tight manner, and that these reactants can be used either individually or in a connected array in flow-through apparatuses for the synthesis of organic products.

* * * * *